United States Patent [19]

Marui et al.

[11] Patent Number: 5,378,608

[45] Date of Patent: Jan. 3, 1995

[54] ENZYME IMMUNOASSAY FOR ANTIGEN AND SOLID PHASE USED THEREFOR

[75] Inventors: Yoji Marui, Takarazuka; Chozo Hayashi, Nishinomiya; Shigeki Ito, Mishima; Mieko Fujio, Ibaraki; Hiroki Tanaka, Osaka; Toshihide Nagasaki, Takarazuka; Yasuji Soda, Kobe; Hitoshi Kaneta, Takatsuki, all of Japan

[73] Assignee: Nippon Shoji Kabushiki Kaisha, Osaka, Japan

[21] Appl. No.: 542,038

[22] Filed: Jun. 22, 1990

[30] Foreign Application Priority Data

Jun. 29, 1989 [JP] Japan .................................. 1-167697
Mar. 20, 1990 [JP] Japan .................................. 2-70341

[51] Int. Cl.$^6$ .................... G01N 33/53; G01N 33/537
[52] U.S. Cl. ........................................ 435/7.5; 435/7.9; 435/7.92; 435/7.94; 436/512
[58] Field of Search ................ 435/7.5, 7.94, 7.9, 435/7.92; 436/512, 518

[56] References Cited

U.S. PATENT DOCUMENTS

| | | | |
|---|---|---|---|
| 4,282,287 | 8/1981 | Giese | 428/407 |
| 4,298,685 | 11/1981 | Parikh et al. | 435/7.5 |
| 4,429,008 | 1/1984 | Martin et al. | 428/402.2 |
| 4,496,654 | 1/1985 | Katz et al. | 435/7.5 |
| 4,778,751 | 10/1988 | Shami et al. | 435/7 |
| 4,798,795 | 1/1989 | Sigler | 435/177 |
| 4,935,339 | 6/1990 | Zahradnik | 435/5 |

FOREIGN PATENT DOCUMENTS

| | | |
|---|---|---|
| 0077671 | 4/1983 | European Pat. Off. |
| 0311768 | 4/1989 | European Pat. Off. |
| WO8704794 | 8/1987 | WIPO |
| WO9004786 | 5/1990 | WIPO |

OTHER PUBLICATIONS

Y. Hiller et al., Methods in Enzymology, vol. 184, pp. 68–71 (1990).
F. Finn et al., The J. of Biol. Chem., vol. 255, No. 12, pp. 5742–5746 (1980).
D. Gretch et al., Anal. Biochem., vol. 163, pp. 270–277 (1987).
M. Colomb et al., Biochem. J., vol. 145, pp. 177–183 (1975).
P. Parham, The J. of Immunology, vol. 131, No. 6, pp. 2895–2902 (1983).
Pierce Product Catalog, 1988, p. 217.
Goding, J. W. *Monoclonal Antibodies: Principles and Practice* p. 118 Academic Press, New York, N.Y. 1983.
Su-Ming Hsu et al., "Use of Avidin–Biotin Peroxidase Complex (ABC) In Immunoperoxidase Techniques . . . ", J. Histochem. Cytochem., vol. 29, No. 4, pp. 577–580, 1981.
Chikashi Tokuda et al., "English Translation of Report in the Program Abstract, General Subject No. 41 of the Proceeding of the 28th Annual Mtg. of Japan Society Clinical Chemistry".
Meir Wilcheck et al., "The Avidin–Biotin Complex in Bioanalytical Applications", Analytical Biochemistry, vol. 171, pp. 1–32 (1988).
Edward A. Bayer et al., "3-(N-Maleimido-propionyl) Biocytin: A Versatile Thiol-Specific Biotinylating Reagent", Analytical Biochemistry, vol. 149, pp. 529–536 (1985).

*Primary Examiner*—Toni R. Scheiner
*Attorney, Agent, or Firm*—Wegner, Cantor, Mueller & Player

[57] ABSTRACT

An enzyme immunoassay for an antigen using a solid phase, which employs (a) a biotinylated antibody in which a biotin derivative is bound to a thiol group of an Fab' fragment of an antibody, (b) an enzyme-labelled antibody, and (c) a solid phase immobilized with a substance capable of specifically reacting with the above biotin derivative selected from the group consisting of avidin, streptoavidin and a derivative thereof which is bound to the solid phase directly or via a linkage between another biotin derivative and a high molecular weight substance bound to the solid phase, or alternatively employs (a') a solid phase immobilized with a biotinylated antibody via a substance selected from the group consisting of avidin, streptoavidin and a derivative thereof wherein said substance is bound to the biotin moiety of said biotinylated antibody and is also bound to the solid phase directly or via a linkage between another biotin derivative and a high molecular weight substance bound to the solid phase, and (b') an enzyme-labelled antibody, and a solid phase used therefor.

3 Claims, 10 Drawing Sheets

ENZYME IMMUNOASSAY FOR ANTIGEN AND SOLID PHASE USED THEREFOR

The present invention relates to a method for measuring an amount of an antigen in a sample and a solid phase used therefor. More particularly, the present invention relates to an enzyme immunoassay for measuring an amount of an antigen in a sample which comprises reacting an antigen in a sample either with a biotinylated antibody, an enzyme-labelled antibody and an avidin-immobilized solid phase or with an enzyme-labelled antibody and a biotinylated antibody-bound avidin-immobilized solid phase to form a biotinylated antibody/antigen/enzyme-labelled antibody complex on the avidin-immobilized solid phase, and measuring an enzyme activity on the solid phase, and a solid phase used therefor.

PRIOR ART

In a modern medical field, it has become more and more important to measure a trace substance such as a tumor marker or a hormone. Since measurement of such a trace substance requires high specificity and sensitivity, an immunological method utilizing an antigen-antibody reaction which is endowed with high specificity and sensitivity has widely been used. There have been known various immunological methods including a fluorescent antibody method, a radioimmunoassay, an enzyme immunoassay and the like. Among others, the enzyme immunoassay where an enzyme is used for labelling has advantages such as a wide range of application, easiness in handling of reagents, capability of treating a large number of a sample, etc. and is becoming a dominant method for measuring a trace substance.

In the enzyme immunoassay for measuring an amount of an antigen, a sandwich method has widely been used where in order to separate an enzyme-labelled antibody reacted with an antigen in a sample and an unreacted enzyme-linked antibody from each other (hereinafter referred to as "B/F separation") the reaction solution is further subjected to an antigen-antibody reaction with an antibody immobilized on a solid phase and after a B/F separation the activity of an enzyme bound to the solid phase is measured. However, the antigen-antibody reaction on a solid phase in such a B/F separation requires a long period of time for equilibrium, which results in time-consuming in measurement and makes the method unsuitable in the field of clinical chemistry where rapid and short-time measurement is required. In recent years, it has been contemplated to use another specific reaction such as avidin-biotin reaction in place of an antigen-antibody reaction in order to conduct the reaction on a solid phase more speedy.

The application of such specific binding of avidin-biotin to the immunological procedure is well known in histochemistry as described in, for example, Anderson, G. W. et al., *J. Amer. Chem. Soc.* 86:1839 (1964). In this method, a biotinylated antibody is bound to, for example, an antigen in a tissue, and an avidin-labelled enzyme is further reacted therewith to form a antibody/biotin-/avidin/enzyme complex in said tissue, and then localization of an antigen in said tissue is determined from the resulting enzyme reaction product. However, this method can not be used for the measurement of an antigen in a sample.

Japanese Patent First Publication No. 229368/1988 discloses the application of the avidin-biotin reaction for a B/F separation in the field of clinical chemistry. This method comprises reacting an antibody to be determined with a labelled antigen, a biotinylated antigen and an avidin-immobilized solid phase to form an avidin/biotinylated antigen/antibody/labelled antigen complex on the solid phase and measuring the label to determine an amount of the antibody.

On the other hand, as a reagent suitable for measuring an amount of an antigen using the avidin-biotin reaction, there is commercially available a reagent for measuring ferritin from Nippon Mediphysics Co. Ltd., which comprises an avidin-immobilized solid phase, a biotinylated antibody and an antibody labelled with a radioisotope. However, the measurement with this reagent still takes a long time as 3 to 4 hours. A similar method has been reported in the Program Abstract, general subject No. 41 of the Proceeding of the 28th Annual Meeting of Japan Society Clinical Chemistry held on Nov. 18 and 19, 1988. This method comprises adding an enzyme-labelled antibody and a biotinylated antibody to a sample containing an antigen to conduct the antigen-antibody reaction in a liquid phase, adding thereto an avidin-immobilized solid phase to allow the resulting sandwich complex of enzyme-labelled antibody/antigen/biotinylated antibody to be adsorbed to the solid phase, and measuring the enzyme activity to determine an amount of the antigen.

In this method, the antigen-antibody reaction proceeds in the liquid phase, and hence, reaches to equilibrium rapidly and further the avidin-biotin reaction on the solid phase proceeds more rapidly than the antigen-antibody reaction on the solid phase, which shortens the reaction time. In this method, there is also used a fluorescent substance to compensate the insufficiency of sensitivity due to the shortening of the reaction time (to about 10 minutes). However, it does still not give a substantial solution of the problem of insufficient sensitivity because the antibody titer is possibly damaged since the biotinylated antibody is prepared by linking a biotin derivative to an amino group of an antibody and further an amount of avidin on the solid phase is possibly deficient due to difficulty in linking avidin to the solid phase.

BRIEF DESCRIPTION OF THE INVENTION

Under the circumstances, the present inventors have intensively studied as to preparation of the biotinylated antibody without deteriorating the antibody titer and as to means for increasing an amount of avidin on the solid phase in order to overcome the problem of insufficient sensitivity as mentioned above, and as a result, have found that the first problem can be solved by linking the biotin derivative to a thiol group of an Fab' fragment of the antibody and the second problem can be solved by linking avidin to the solid phase via a biotinylated high molecular weight substance to increase sensitivity, that the sensitivity can be further increased if both means are used together, that even when a conventional biotinylated antibody and avidin-immobilized solid phase are used, the sensitivity can be increased if they are used in the form of a biotinylated antibody-bound avidin-immobilized solid phase in which said biotinylated antibody is bound to the avidin-immobilized solid phase, and that this latter method can advantageously be carried out for the measurement of an antigen only by addition of the enzyme-labelled antibody, which is advantageous in view of easier procedure of the method.

An object of the present invention is to provide an enzyme immunoassay for an antigen using a solid phase, which employs (a) a biotinylated antibody in which a biotin derivative is bound to a thiol group of an Fab' fragment of an antibody, (b) an enzyme-labelled antibody, and (c) an avidin-immobilized solid phase, i.e. a solid phase immobilized with a substance capable of specifically reacting with the above biotin derivative selected from the group consisting of avidin, streptoavidin and a derivative thereof (this assay being hereinafter referred to as "Immunoassay I").

Another object of the invention is to provide an enzyme immunoassay for an antigen using a solid phase, which employs (a') a biotinylated antibody-immobilized solid phase, i.e. a solid phase immobilized with a biotinylated antibody via a substance selected from the group consisting of avidin, streptoavidin and a derivative thereof wherein said substance is bound to the biotin moiety of said biotinylated antibody and is also bound to the solid phase, and (b') an enzyme-labelled antibody (this assay being hereinafter referred to as "Immunoassay II").

Another object of the invention is to provide Immunoassay I wherein said solid phase (c) is a solid phase immobilized with a substance capable of specifically reacting with a biotin derivative selected from the group consisting of avidin, streptoavidin and a derivative thereof wherein the substance such as avidin is immobilized to the solid phase via a linkage between another biotin derivative and a high molecular weight substance [e.g. bovine serum albumin (hereinafter referred to as "BSA")] bound to said solid phase.

Another object of the invention is to provide Immunoassay I which is carried out by reacting the biotinylated antibody (a) and the enzyme-labelled antibody (b) with an antigen to be determined in a sample to form a biotinylated antibody/antigen/enzyme-labelled antibody complex, and then reacting said complex with the substance selected from the group consisting of avidin, streptoavidin and a derivative thereof immobilized on said solid phase (c).

Another object of the invention is to provide Immunoassay I which is carried out by simultaneously reacting the biotinylated antibody (a), the enzyme-labelled antibody (b), a sample containing an antigen to be determined and the solid phase (c).

A further object of the invention is to provide Immunoassay II wherein said biotinylated antibody-immobilized solid phase (a') is a solid phase immobilized with a biotinylated antibody via a substance selected from the group consisting of avidin, streptoavidin and a derivative thereof wherein said substance is bound to the biotin moiety of the biotinylated antibody and is also bound to the solid phase via a linkage between another biotin derivative and a high molecular weight substance (e.g. BSA) bound to said solid phase.

Further object of the invention is to provide Immunoassay II wherein said biotinylated antibody is an antibody in which a biotin derivative is bound to a thiol group of an Fab' fragment of the antibody.

Still further object of the invention is to provide Immunoassay II which is carried out by simultaneously reacting the enzyme-labelled antibody (b'), a sample containing an antigen to be determined and the solid phase (a').

Still another object of the invention is to provide a solid phase for enzyme immunoassay which comprises a solid phase immobilized with a substance capable of specifically reacting with a biotin derivative selected from the group consisting of avidin, streptoavidin and a derivative thereof wherein said substance is immobilized to the solid phase via a linkage between another biotin derivative and a high molecular weight substance (e.g. BSA) bound to said solid phase (hereinafter referred to as "Solid Phase I").

Still further object of the invention is to provide a solid phase for enzyme immunoassay which comprises a solid phase immobilized with a biotinylated antibody via a substance capable of specifically reacting with a biotin derivative selected from the group consisting of avidin, streptoavidin and a derivative thereof wherein said substance is bound to the biotin moiety of the biotinylated antibody and is also bound to the solid phase directly or via a linkage between another biotin derivative and a high molecular weight substance bound to the solid phase (hereinafter referred to as "Solid Phase II").

These and other objects and advantages of the invention will be apparent to those skilled in the art from the following description.

DETAILED DESCRIPTION OF THE INVENTION

Solid Phase I of the present invention has a structure wherein a solid phase is immobilized with a high molecular weight substance/biotin/avidin (or streptoavidin or a derivative thereof) complex, in which a high molecular weight substance is biotinylated and avidin, streptoavidin or a derivative thereof is bound to the biotinylated moiety thereof, in other words, a structure wherein avidin, streptoavidin or a derivative thereof is immobilized to a solid phase via the biotinylated high molecular weight substance. Solid Phase II of the present invention has a structure wherein the biotinylated antibody is bound to Solid Phase I of the present invention at the moiety of avidin, etc. thereon, or to a solid phase to which a substance selected from the group consisting of avidin, streptoavidin and a derivative thereof is directly bound, through avidin-biotin linkage.

Solid Phase I of the present invention can be prepared by, for example, biotinylating a high molecular weight substance with a biotin derivative (hereinafter referred to as "biotinylating reagent"), linking said biotinylated high molecular weight substance to a solid phase via the high molecular weight substance moiety thereof and further linking avidin, streptoavidin or a derivative thereof (e.g. a neutralized avidin in which free amino group(s) is/are pre-blocked by, for example, acetylation with acetic anhydride) to the biotin moiety. The high molecular weight substance can be bound to the solid phase by various methods including physical adsorption, covalent bonding and the like.

Solid Phase II of the present invention can be prepared by, for example, linking a conventional biotinylated antibody or a biotinylated antibody in which the biotin derivative is bound to a thiol group of an Fab' fragment of an antibody to Solid Phase I of the present invention or to a solid phase to which avidin, streptoavidin or a derivative thereof is directly bound, through avidin-biotin linkage.

The high molecular weight substance used in the present invention has a functional group reactive with the biotinylating reagent and is capable of being physically adsorbed or covalently bound to the solid phase, including proteins [e.g. BSA, ovalbumin (hereinafter referred to as "OA"), immunoglobulin, collagen, gelatin, casein, etc.], polysaccharides (e.g. dextran, pullulan, etc.) and the like.

The biotinylating reagent used in the present invention is a biotin derivative having a functional group reactive with the high molecular weight substance to form a covalent bond and includes, for example, biotin-N-hydroxysuccinimide ester (hereinafter referred to as "NHS-biotin"), N-biotinyl-6-aminocaproyl-N-hydroxysulfosuccinimide ester (hereinafter referred to as "NHS-LC-biotin"), sulfosuccinimidyl-2-(biotinamido)ethyl-1, 3-dithiopropionate (hereinafter referred to as "NHS-SS-biotin"), and the like [cf. Analytical Biochemistry: 171, 1–32 (1988)].

The biotinylating reagent and the high molecular weight substance can be bound to each other by reacting one mole of the high molecular weight substance with preferably about 1 to about 100 moles of the biotinylating reagent, depending on a kind of the biotinylating reagent and the high molecular weight substance. The reaction can be conducted under such conditions that the high molecular weight substance and the biotinylating reagent are bound to each other sufficiently and the moiety on the high molecular weight substance where the solid phase is bound is not inactivated, for example, under the conditions of pH of the solution ranging from about 4 to about 10, the reaction temperature of about 4° to about 45° C. and the reaction time of about 10 minutes to about 24 hours.

The thus prepared biotinylated high molecular weight substance can be bound to the solid phase by the usual method such as the physical adsorption or the covalent bond but the method should not interfere the bond between the biotin moiety of the resulting biotinylated high molecular weight substance-immobilized solid phase and avidin, streptoavidin or a derivative thereof. For example, the method for physical adsorption can be carried out by immersing the solid phase into a buffered solution of the biotinylated high molecular weight substance (1 to 1000 μg/ml). The method for covalent bonding can be carried out by, for example, reacting the biotinylated high molecular weight substance in the form of a buffered solution (1 to 1000 μg/ml; pH 5 to 7) with a solid phase containing carboxyl group which is pretreated with a buffered solution of 1-ethyl-3-(3-dimethylaminopropyl)carbodiimide hydrochloride (5 to 200 mg/ml) for 1 to 24 hours.

The resulting solid phase to which the biotinylated high molecular weight substance is bound is then immersed into a buffered solution of avidin, streptoavidin or a derivative thereof (1 to 1000 μg/ml) for 1 to 20 hours to give Solid Phase I of the present invention.

Solid Phase II of the present invention can be prepared from Solid Phase I of the present invention or a solid phase which is prepared by immersing a conventional solid phase into a buffered solution of avidin, streptoavidin or a derivative thereof (1 to 1000 μg/ml) for 1 to 20 hours, that is, by immersing the solid phase into a buffered solution of the biotinylated antibody (1 to 1000 picomoles/ml) for 1 to 20 hours.

The solid phase material used in Solid Phases I and II of the present invention may be any conventional material which can immobilize the complex stably and has a shape suitable for washing and measurement, including beads, plate, test tube, latex etc. made of polystyrene, polypropylene, polyvinyl chloride, glass, ceramics, agarose and the like, or any other substances conventionally used in enzyme immunoassay procedures.

The present invention also provides a sandwich immunoassay for an antigen using the biotinylated antibody, the enzyme-labelled antibody and the solid phase to which avidin, streptoavidin or a derivative thereof is immobilized wherein said biotinylated antibody is an antibody in which the biotin derivative is bound to a thiol group of the Fab' fragment of the antibody. Such biotinylated antibody can be prepared by firstly producing the Fab' fragment in accordance with the known method, e.g. the method described in "Zoku Seikagaku Jikken Koza 5 Men-eki Seikagaku Kenkyuho (Biochemical Experiment Course, second series, Volume 5, Method of Study in Immunological Biochemistry)", Tokyo Kagaku Dojin, 1986, pages 89–112, and then linking the biotin derivative to thiol group of the Fab' fragment.

The biotin derivative used in the above procedure for preparing the biotinylated antibody is a biotinylating reagent having a functional group reactive with a thiol group such as iodoacetyl group or maleimide group, including N-iodoacetyl-N-biotinylhexylenediamine, 3-(N-maleimidobutyryl)biocytin (MBB), 3-(N-maleimidopropionyl)biocytin, 3-(N-maleimidocaproyl)-biocytin, N-biotinyl-N-(6-maleimidohexanoyl)hydrazide, and the like.

An amount of the Fab' fragment and the biotinylating reagent used in the above reaction may vary depending on a kind of the biotinylating reagent but preferably about 5 to about 20 moles amount of the biotinylating reagent is used per one mole of the Fab' fragment. The reaction is carried out under such conditions that the Fab' fragment and the biotinylating reagent are bound to each other sufficiently and the antibody titer is not deteriorated, for example, under the conditions of pH of the solution ranging from about 6 to about 7, the reaction temperature of about 4° to about 40° C., preferably about 20° to about 30° C., and the reaction time of about 1 to about 24 hours.

According to Immunoassay I of the present invention, the biotinylated antibody as prepared above is used in the sandwich immunoassay for an antigen wherein a mixture (50 to 1000 $\mu$l, preferably 100 to 500 $\mu$l) of the above biotinylated antibody and the enzyme-labelled antibody is added to a sample solution (1 to 100 $\mu$l, preferably 5 to 50 $\mu$l) to form a biotinylated antibody/antigen/enzyme-labelled antibody complex (reaction 1), and thereto is further added the solid phase where avidin, streptoavidin or a derivative thereof is immobilized (reaction 2). In the above immunoassay, all the reagents, i.e. the sample, the biotinylated antibody, the enzyme-labelled antibody and the solid phase where avidin, streptoavidin or a derivative thereof is immobilized can also be added simultaneously so that the above two reactions are carried out at the same time, allowing to conduct the immunoassay in a single step.

The solid phase to which avidin, streptoavidin or a derivative thereof is immobilized used in the above immunoassay may be either the known avidin-immobilized solid phase to which avidin, streptoavidin or a derivative thereof is directly immobilized, including immobilized avidin D manufactured by Vector Laboratories, Inc., the solid phase disclosed in Japanese Patent First Publication No. 229368/-1988, and the like, or Solid Phase I of the present invention. Solid Phase I of the present invention allows for more stable measurement of the antigen and hence is preferable.

According to Immunoassay II of the present invention, Solid Phase II of the present invention, in which the biotinylated antibody prepared as mentioned above or the conventional biotinylated antibody is previously bound to Solid Phase I of the present invention or the solid phase to which avidin, streptoavidin or a derivative thereof is directly immobilized, is used in the immunoassay for an antigen. In this case, a sample solution (1 to 100 $\mu$l, preferably 5 to 50 $\mu$l) and a buffered solution of the enzyme-labelled antibody (50 to 1000 $\mu$l, preferably 100 to 500 $\mu$l) are added to Solid Phase II to form an antigen/enzyme-labelled antibody complex on the solid phase.

The reaction time in the above immunoassay is about 1 to about 20 minutes, preferably about 5 to about 15 minutes for each reaction of the antigen-antibody reaction and the avidin-biotin reaction when Solid Phase I of the present invention is used. In case of the single step procedure to conduct the reactions simultaneously, the reaction time may be about 1 to about 30 minutes, preferably about 5 to about 20 minutes. When Solid Phase II of the present invention is used, the antigen-antibody reaction may be carried out for about 1 to about 30 minutes, preferably about 5 to about 20 minutes.

After completion of the reaction, the solid phase is washed and a substrate solution (50 to 1000 $\mu$l, preferably 100 to 500 $\mu$l) is added, followed by enzyme reaction for 1 to 30 minutes, preferably 5 to 20 minutes, in case of colorimetry, or for 15 seconds to 15 minutes, preferably 1 to 5 minutes, in case of fluorometry. After completion of the reaction, the reaction solution is directly, or after addition of an appropriate amount of a reagent for terminating the reaction, subjected to colorimetry or fluorometry. A concentration of the antigen in the sample is then calculated from a calibration curve which has previously been prepared using antigen solutions of known concentration.

The above all reactions are carried out at 10° to 45° C., preferably at 20° to 40° C. The biotin-avidin reaction and the antigen-antibody reaction are carried out at pH 5 to 9, preferably at around neutral pH, and the enzyme activity is measured at around optimal pH to the enzyme for labelling.

The enzyme for labelling may be any enzyme which is usually employed in enzyme immunoassay and includes, for example, $\beta$-D-galactosidase ($\beta$-Gal), peroxidase (POD), alkaliphosphatase (ALP), and the like. Measurement of the enzyme activity on the solid phase is conducted by adding a suitable amount of substrate to the reaction system and then measuring the enzyme activity by the conventional method such as colorimetry or fluorometry. The substrate employed in the measurement of the enzyme activity includes ortho-nitrophenyl-$\beta$-D-galactopyranoside, 4-methylumbelliferyl-$\beta$-D-galactopyranoside, etc. in case of the labelling enzyme being $\beta$-Gal; hydrogen peroxide with 2,2'-azino-bis(3-ethylbenzothiazoline-6-sulfonic acid) (ABTS), hydrogen peroxide with 3,3',5,5'-tetramethylbenzidine, hydrogen peroxide with o-phenylenediamine, etc. in case of POD; paranitrophenylphosphoric acid, (4-methyl)umbelliferylphosphoric acid, etc. in case of ALP.

In accordance with the method of the present invention, an amount of the antigen present in a sample such as human serum, plasma, urine etc. can be measured with a high sensitivity and in an extremely short period of time. By combining the method and the solid phase of the present invention, the sensitivity is more improved and the desired immunoassay can be effected more suitably.

The present invention is illustrated in more detail by the following Examples, Preparation and Comparative Examples but should not be construed to be limited thereto.

EXAMPLE 1 [Preparation of biotinylated antibody (biotin-Fab')]

(a) Preparation of monoclonal antibody against α-fetoprotein (AFP):

A hybridoma was prepared by a polyethylene glycol method using spleen cells of BALB/c mouse immunized with AFP and mouse myeloma cells FO. The obtained hybridoma was cloned twice by a limiting dilution method to give anti-AFP monoclonal antibody-producing hybridoma NHAFP-14. This hybridoma was cultured on ASF culture medium 103 (manufactured by Ajinomoto K.K.) and an anti-AFP monoclonal antibody (MNHAFP-14) was purified from the culture supernatant using protein A-agarose column.

(b) Preparation of Fab':

The anti-AFP-monoclonal antibody solution (MNHAFP-14; 10 mg/2 ml) obtained in the above process (a) was dialyzed against 0.1M acetate buffer (pH 4.2), thereto was added a pepsin solution (manufactured by Boehringer Mannheim GmbH; 20 mg/ml 0.1M acetate buffer; 100 μl) and the mixture was reacted at 37° C. for 20 hours. The reaction solution was centrifuged and the supernatant was subjected to Sephacryl-S-200 column (φ1.5 cm×50 cm, eluent: 0.1M phosphate buffer, pH 6.0) to give an F(ab')₂ fraction. To the F(ab')₂ fraction was added 2-mercaptoethylamine hydrochloride at a final concentration of 10 mmol/l and the mixture was reacted at 37° C. for 1 hour. The reaction solution was centrifuged and the supernatant was subjected to Sephacryl-S-200 column (φ1.5 cm×50 cm, eluent: 0.1M phosphate buffer, pH 6.0) to give an Fab' fraction.

(c) Preparation of biotinylated antibody (biotin-Fab'):

In accordance with the method described in Anal. Biochem. 149, 529–536 (1985), 3-(N-maleimidobutyryl)-biocytin (MBB) was synthesized. To the Fab' (1.66 mg/1.3 ml) prepared in the above process (a) was added the MBB solution (0.5 mg/ml in 0.1M phosphate buffer, pH 6.0; 0.5 ml) and the mixture was reacted at room temperature for 2 hours. The reaction solution was centrifuged and the supernatant was subjected to Sephadex-G-25 column (φ1.5 cm×30 cm, eluent: 0.1M phosphate buffer, pH 6.0) to give the desired biotin-Fab'.

EXAMPLE 2 [Preparation of enzyme-labelled antibody (POD-Fab')]

(a) Preparation of anti-AFP monoclonal antibody:

In the same manner as described in Example 1 (a), there was prepared an anti-AFP monoclonal antibody (MNHAFP-18).

(b) Preparation of Fab':

Using the anti-AFP monoclonal antibody (MNHAFP-18) obtained in the above process (a), the procedure in Example 1 (b) was repeated to give the Fab'.

(c) Preparation of POD-maleimide:

POD (manufactured by Boehringer Mannheim GmbH; 6 mg) was dissolved in 0.1M phosphate buffer (0.8 ml; pH 7.0), and thereto was added N-(γ-maleimidobutyryloxy)succinimide (manufactured by Dojin Kagaku K. K.; 80 mg/ml N,N'-dimethylformamide; 50 μl) and the mixture was reacted at 30° C. for 1 hour. The reaction solution was centrifuged and the supernatant was subjected to Sephadex G-25 column (φ1.5 cm×30 cm, eluent: 0.1M phosphate buffer, pH 6.0) to give a POD-maleimide fraction.

(d) Preparation of POD-Fab':

To the Fab' (1 mg) prepared in the above process (b) was added the POD-maleimide (1 mg) prepared in the above process (c) and the mixture was reacted in a cold chamber for 20 hours. The reaction solution was centrifuged and the supernatant was subjected to Sephacryl-S-200 column (φ1.5 cm×50 cm, eluent: 0.1M phosphate buffer, pH 6.5) to give the desired POD-Fab' fraction.

Preparation (Preparation of conventional avidin-immobilized solid phase)

Avidin (manufactured by Wako Jun-yaku K.K.; an agent for biochemistry, 5 mg) was dissolved in 20 mM carbonate buffer (pH 9.6, containing 0.15M sodium chloride; 10 ml). About 30 polystyrene beads (type C, manufactured by Sumitomo Bakelite Co., Ltd., as a solid phase) were added to the above solution and allowed to stand at room temperature for 20 hours to adsorb avidin onto the solid phase. This solid phase was washed with a physiological saline solution several times, immersed into 1% bovine serum albumin (BSA) solution (in 0.1M phosphate buffer, pH 7.0) and then allowed to stand at room temperature for 20 hours to give the desired avidin-immobilized solid phase.

EXAMPLE 3 [AFP immunoassay using biotin-Fab' (2 steps)]

Figure 1:
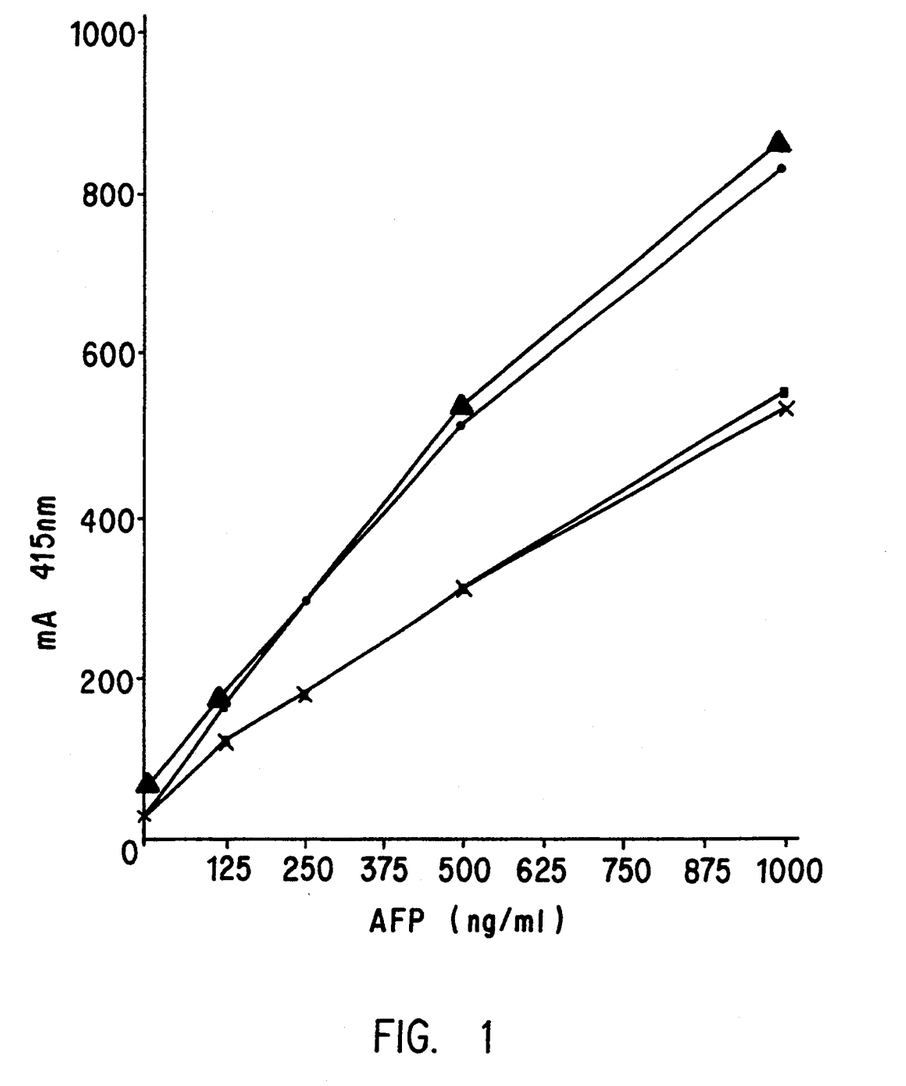
FIG. 1 is a calibration curve for an antigen (AFP) in a sample measured by enzyme immunoassay using a biotin-Fab' or a biotin-IgG in which the sensitivity in case of the biotin-Fab' and the sensitivity in case of the biotin-IgG are compared to each other.

Human AFP (manufactured by Daco Co.) was dissolved in human serum with no AFP and the solution was adjusted to AFP concentrations ranging from 0 to 1000 ng/ml. This sample (50 μl) was added to a test tube, and thereto was added an antibody solution (400 μl) which was prepared by adding 10 mM phosphate buffer (pH 7.0, containing 0.15M sodium chloride and 0.5% BSA) to a mixture of the biotin-Fab' (Fab' concentration of 160 μg/ml; 50 μl) and the POD-Fab' (POD activity of 26.1 IU/ml; 500 μl) so that the total volume became 10 ml, and the mixture was incubated at 37° C. for 10 minutes. Thereafter, to the reaction solution was added the avidin-immobilized solid phase prepared in the Preparation and the mixture was incubated at 37° C. for 10 minutes. After completion of the reaction, the reaction solution was removed by suction, and a washing solution (physiological saline; 2 ml) was added to the solid phase and, after shaking, the washing solution was removed by suction. This washing procedure was repeated further two times. After washing, a substrate solution (ABTS 1 mg/ml, 0.01% hydrogen peroxide, 0.1M citrate buffer, pH 4.2; 500 μl) was added to the resulting solid phase, and the mixture was reacted at 37° C. for 15 minutes. To the mixture was added 5 mM sodium azide (2 ml) as a reaction terminater and the absorbance at 415 nm was measured. The results are shown in FIG. 1 as a circle.

EXAMPLE 4 [AFP immunoassay using biotin-Fab' (1 step)]

The sample (50 μl) prepared in Example 3 was added to a test tube, and thereto were added the avidin-immobilized solid phase prepared in the Preparation and further the same antibody solution (400 μl) as used in Example 3, and the mixture was incubated at 37° C. for 10 minutes. After completion of the reaction, the reaction solution was removed by suction, and to the solid phase was added the same washing solution (2 ml) as used in Example 3. After shaking, the washing solution was removed by suction. The washing procedure was repeated further two times. After the washing, the same substrate solution (500 μl) as used in Example 3 was added to the resulting solid phase and the mixture was reacted at 37° C. for 15 minutes. To the mixture was added the same reaction terminater (2 ml) as used in Example 3 and the absorbance at 415 nm was measured. The results are shown in FIG. 1 as a triangle.

COMPARATIVE EXAMPLE 1

The same procedure as in Example 3 was repeated except that a biotinylated antibody in which the biotin derivative was bound to amino group of an antibody, which was prepared by adding an NHS-biotin solution (1 mg/ml DMSO; 300 μl) to an anti-AFP monoclonal antibody solution (MNHAFP-14: 2.5 mg/ml 0.1M phosphate buffer), reacting the mixture at 30° C. for 1 hour and subjecting the reaction solution to Sephadex G-25 column, was employed instead of the biotin-Fab' in Example 3 at the same molar concentration. The results are shown in FIG. 1 as x.

COMPARATIVE EXAMPLE 2

The same procedure as in Example 4 was repeated except that the biotinylated antibody in Comparative Example 1 was employed instead of the biotin-Fab' in Example 4 at the same molar concentration. The results are shown in FIG. 1 as a square.

As is clear from the results shown in FIG. 1, the method using the biotin-Fab' of the present invention has a sensitivity about two times higher than that of the method using the conventional biotinylated antibody in which the biotin derivative is bound to amino group of the antibody.

EXAMPLE 5 (Preparation of Solid Phase I of the present invention)

(a) Preparation of biotin-BSA:

BSA (manufactured by Oriental Yeast K.K., F-V; 30 mg) was dissolved in 0.1M phosphate buffer (pH 7.0; 1 ml), and thereto was added an NHS-SS-biotin solution (manufactured by Pierce Chemical Co., 16.8 mg/ml in 0.1M phosphate buffer, pH 7.0; 1 ml) and the mixture was reacted at 30° C. for 1 hour. The reaction solution was centrifuged and the supernatant was subjected to Sephadex G-25 column ($\phi$1.5 cm×30 cm, eluent: 50 mM carbonate buffer, pH 9.6) to give a biotin-BSA fraction.

(b) Preparation of Solid Phase I of the present invention:

The biotin-BSA prepared in the above process (a) was diluted with 50 mM carbonate buffer (pH 9.6) to adjust the biotin-BSA concentration to 10 μg/ml. This solution (100 μl) was poured into each well of a plate (manufactured by Nunc Co., Immunoplate I, 96-well) and allowed to react at room temperature for 1 hour for immobilization. After washing the wells with a physiological saline solution several times, an avidin solution (Avidin D, manufactured by Vector Laboratories, Inc., 50 μg/ml in 0.1M phosphate buffer, pH 7.0; 100 μl) was poured into each well and allowed to react at 37° C. for 1 hour. After washing the wells with a physiological saline solution several times, 3% BSA solution (in 50 mM carbonate buffer, pH 9.6; 250 μl) was added and treated at 37° C. for 1 hour to give Solid Phase I of the present invention.

EXAMPLE 6 (Preparation of Solid Phase I of the present invention)

(a) Preparation of biotin-OA:

OA (manufactured by Sigma Co., 30 mg) was dissolved in 0.1M phosphate buffer (pH 7.0 , 1 ml), thereto was added an NHS-LC-biotin solution (manufactured by Pierce Chemical Co., 12.6 mg/ml 0.1M phosphate buffer, pH 7.0; 100 μl) and the mixture was reacted at 30° C. for 1 hour. Thereafter, the procedure in Example 5 (a) was repeated to give a biotin-OA fraction.

(b) Preparation of Solid Phase I of the present invention:

The biotin-OA prepared in the above process (a) was diluted with 50 mM carbonate buffer (pH 9.6) to adjust to 10 μg/ml. Thereafter, the procedure in Example 5 (b) was repeated to give Solid Phase I of the present invention.

EXAMPLE 7 (Preparation of Solid Phase I of the present invention)

(a)-Preparation of biotin-immunoglobulin:

Using rabbit IgG, the procedure (the first half) in Example 1 (b) was repeated to give an F(ab')$_2$. To the F(ab')$_2$ (10 mg/ml in 0.1M phosphate buffer, pH 7.0; 3 ml) was then added an NHS-LC-biotin solution (manufactured by Pierce Chemical Co., 15 mg/ml in 0.1M phosphate buffer, pH 7.0; 300 μl) and the mixture was reacted at 30° C. for 1 hour. Thereafter, the procedure in Example 5 (a) was repeated to give a biotin-F(ab')$_2$ fragment. Thereafter, the procedure (the last half) in Example 1 (b) was repeated to give a biotin-Fab'.

(b) Preparation of Solid Phase I of the present invention:

The biotin-Fab' prepared in the above process (a) was diluted with 50 mM carbonate buffer (pH 9.6) to adjust to a concentration of 20 μg/ml. Thereafter, the procedure in Example 5 (b) was repeated to give Solid Phase I of the present invention.

EXAMPLE 8 [Preparation of enzyme-labelled antibody (β-Gal-Fab')]

(a) Preparation of Fab':

Using the anti-AFP monoclonal antibody (MNHAFP-18) prepared in Example 2 (a), the procedure in Example 2 (b) was repeated to give the Fab'.

(b) Preparation of β-Gal-maleimide:

β-Gal (manufactured by Oriental Yeast K.K., 10 mg) was dissolved in 0.1M phosphate buffer (pH 6.0, 2 ml), and thereto was added an o-phenylenedimaleimide solution (manufactured by Aldrich Co., 25 mg/ml in N,N'-dimethylformamide; 100 μl) and the mixture was reacted at 30° C. for 20 minutes. The reaction solution was centrifuged and the supernatant was subjected to Sephadex G-25 column ($\phi$1.5 cm ×30 cm, eluent: 0.1M phosphate buffer, pH 6.0) to give a β-Gal-maleimide fraction.

(c) Preparation of β-Gal-Fab':

To the Fab' (1 mg) prepared in the above process (a) was added the β-Gal-maleimide (3.9 mg) prepared in the process (b) and the mixture was reacted at 30° C. for 30 minutes. The reaction solution was centrifuged and the supernatant was subjected to Sepharose 6B column ($\phi$1.5 cm×50 cm, eluent: 10 mM phosphate buffer, pH 6.5, containing 0.1% BSA) to give a β-Gal-Fab' fragment.

EXAMPLE 9 (AFP immunoassay)

Figure 2:
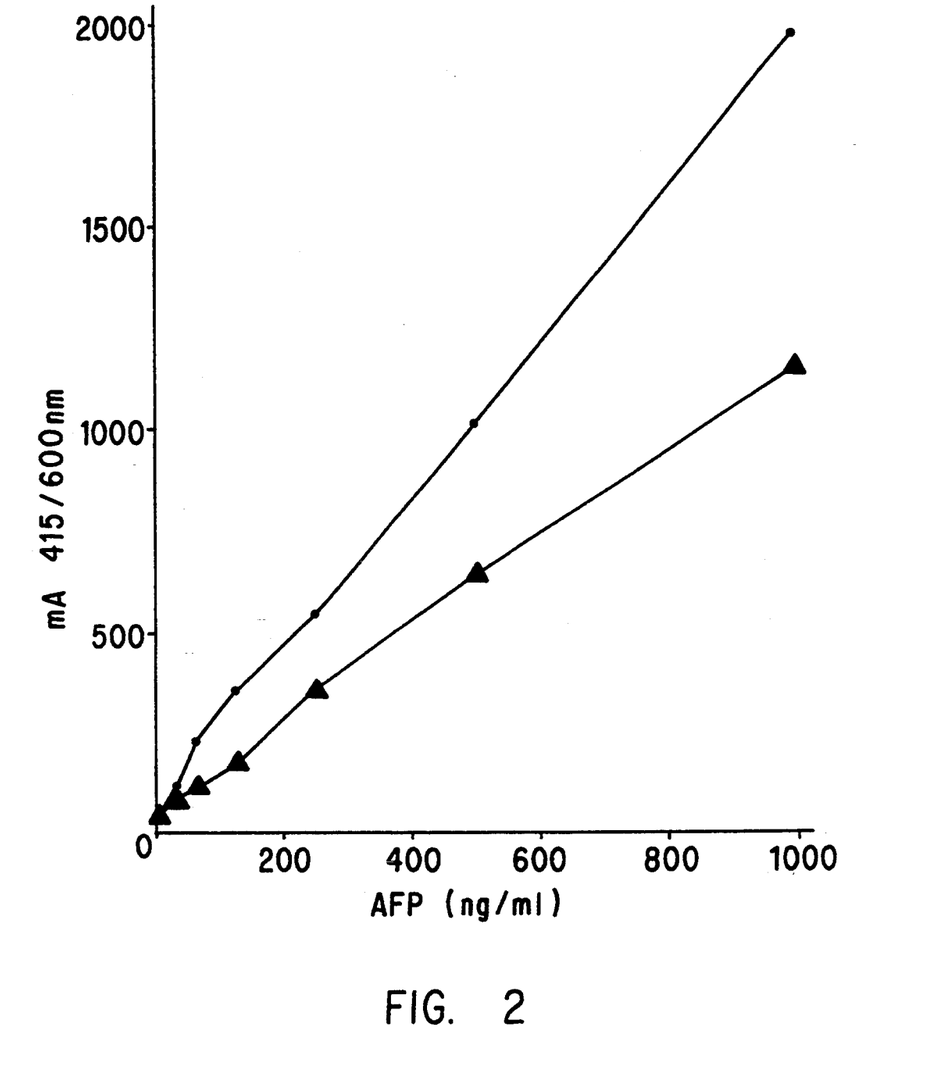
FIG. 2 is a calibration curve for an antigen (AFP) in a sample measured by enzyme immunoassay using Solid Phase I of the present invention employing a biotin-BSA or a conventional avidin-immobilized solid phase in which the sensitivity in case of Solid Phase I of the present invention and the sensitivity in case of the conventional solid phase are compared to each other.

The sample (20 μl) prepared in Example 3 was poured into each well of Solid Phase I of the present invention, and thereto was added an antibody solution (100 μl), and the mixture was incubated at 37° C. for 15 minutes. The antibody solution used in this procedure was prepared by adding 0.01M phosphate buffer (pH 7.0, containing 0.1M sodium chloride and 0.2% BSA) to the biotin-Fab° (16 µg) prepared in Example 1 and the β-Gal-Fab' (20 U) and making the total volume of 10 ml. After completion of the reaction, the reaction solution was removed by suction and then a washing solution (physiological saline solution) was added to the well, followed by removal of the washing solution by suction. This washing procedure was repeated further four times. After washing, a substrate solution [o-nitrophenyl-β-D-galactopyranoside 3.01 g/l in 50 mM phosphate buffer (containing 75 mM sodium chloride, 0.04% $MgCl_2$, 0.05% BSA, 6% ethylene glycol); 100 µl] was added to the resulting well and the mixture was reacted at 37° C. for 10 minutes, and then the reaction was terminated by adding 1% sodium carbonate (100 µl). The absorbances at 415 nm (main) and at 600 nm (sub) were measured. The results are shown in FIG. 2 as a circle.

COMPARATIVE EXAMPLE 3

Figure 3:
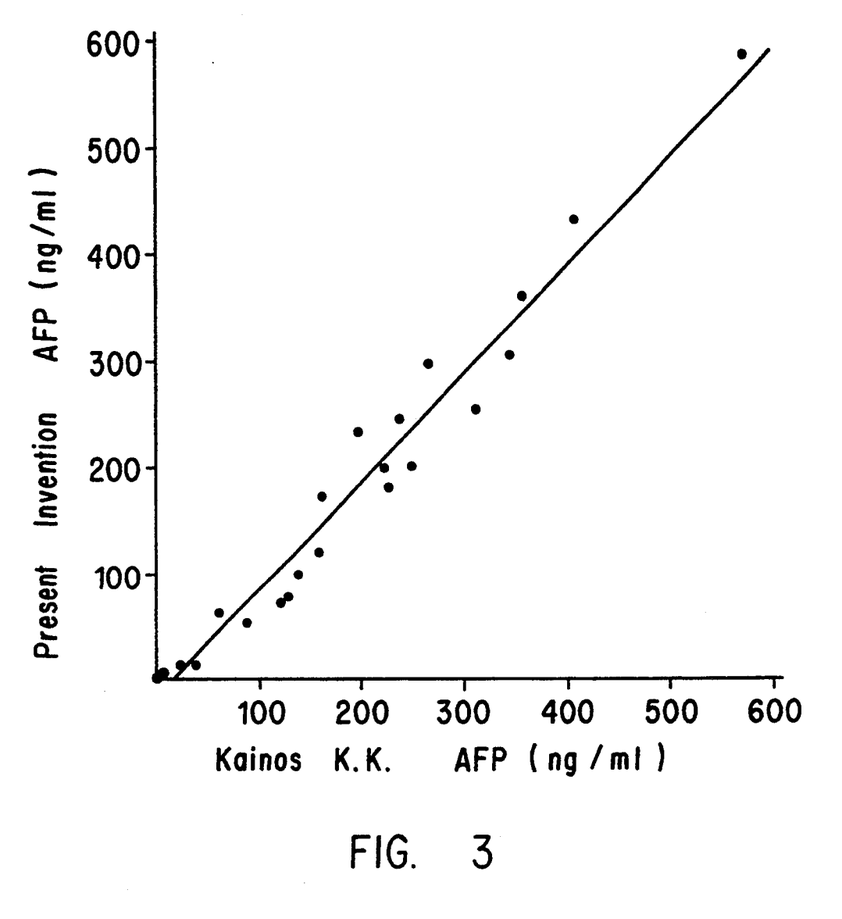
FIG. 3 is a graph showing a correlation between an antigen (AFP) concentrations in a sample measured by the enzyme immunoassay of the present invention using the Solid Phase I employing a biotin-BSA and by a conventional enzyme immunoassay using a commercially available kit.

The procedures in Example 9 were repeated except that the conventional avidin-immobilized solid phase, which was prepared in accordance with the procedure in Example 5 except that the biotin-BSA was not immobilized, was used instead of Solid Phase I of the present invention. The results are shown in FIG. 2 as a triangle. As is clear from the results shown in FIG. 2, the immunoassay using Solid Phase I of the present invention had about 2 times higher sensitivity than that of the immunoassay using the conventional avidin-immobilized solid phase. FIG. 3 shows the correlation between the AFP concentration measured by the immunoassay using Solid Phase I of the present invention and that measured by the conventional enzyme immunoassay (AFP EIA Kit "Mitsui" II commercially available from Kainos K.K.). As is clear from the results shown in FIG. 3, the good correlation was obtained.

EXAMPLE 10 (AFP immunoassay)

AFP immunoassay was conducted using the procedures in Example 9 except that Solid Phases I of the present invention prepared in Examples 6 and 7, in which the biotin-OA and the biotin-Fab' were employed, respectively, were employed instead of Solid Phase I of the present invention prepared in Example 5 and except that the absorbances at 415 nm (main) and at 650 nm (sub) were measured. The results are shown in FIGS. 4 and 5 as a circle, respectively.

The procedure in Comparative Example 3 using the conventional avidin-immobilized solid phase was also repeated to conduct the AFP immunoassay. The results are shown in FIGS. 4 and 5 as a triangle.

Figure 4:
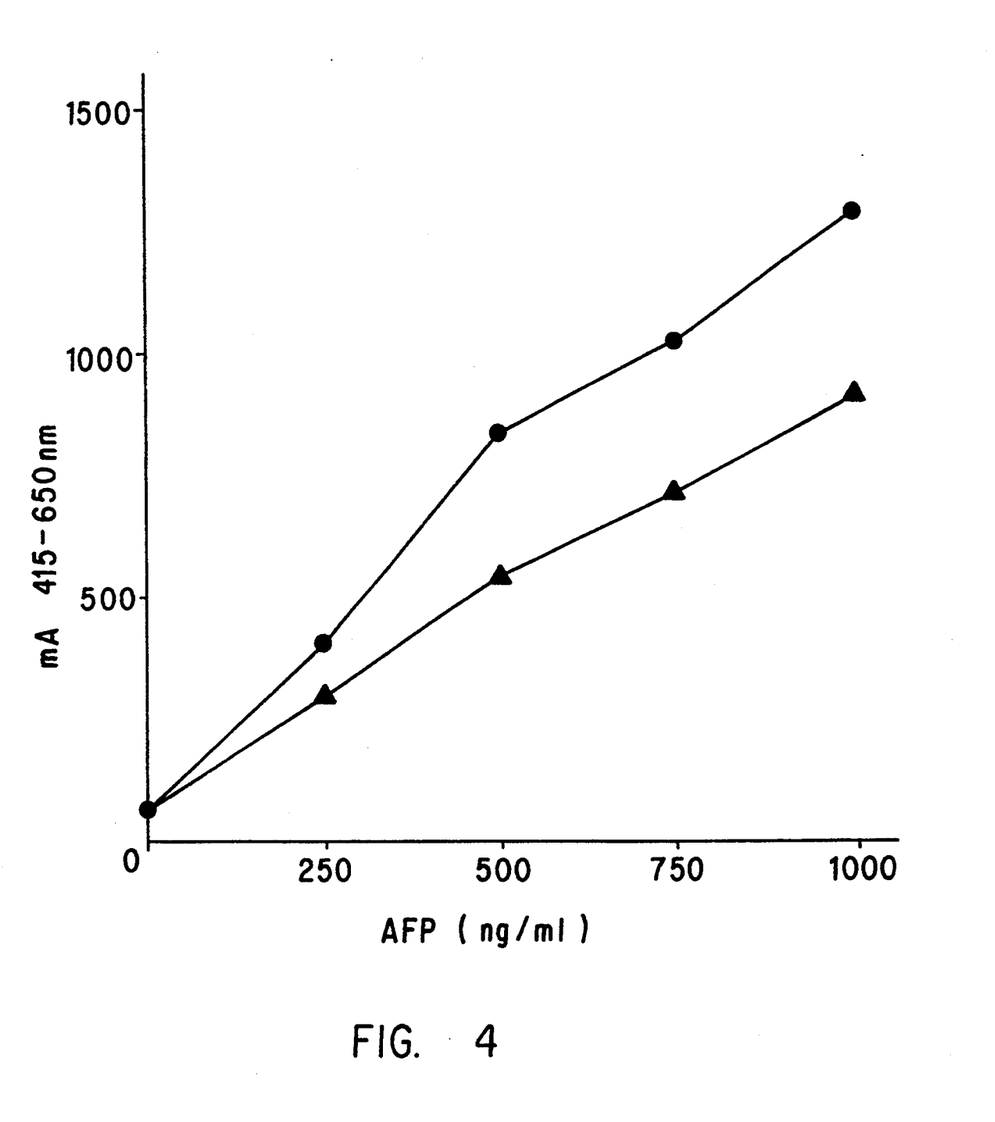
FIG. 4 is a calibration curve for an antigen (AFP) in a sample measured by enzyme immunoassay using Solid Phase I of the present invention employing a biotin-OA (OA means ovalbumin) or a conventional avidin-immobilized solid phase in which the sensitivity in case of Solid Phase I of the present invention and the sensitivity in case of the conventional solid phase are compared to each other.
Figure 5:
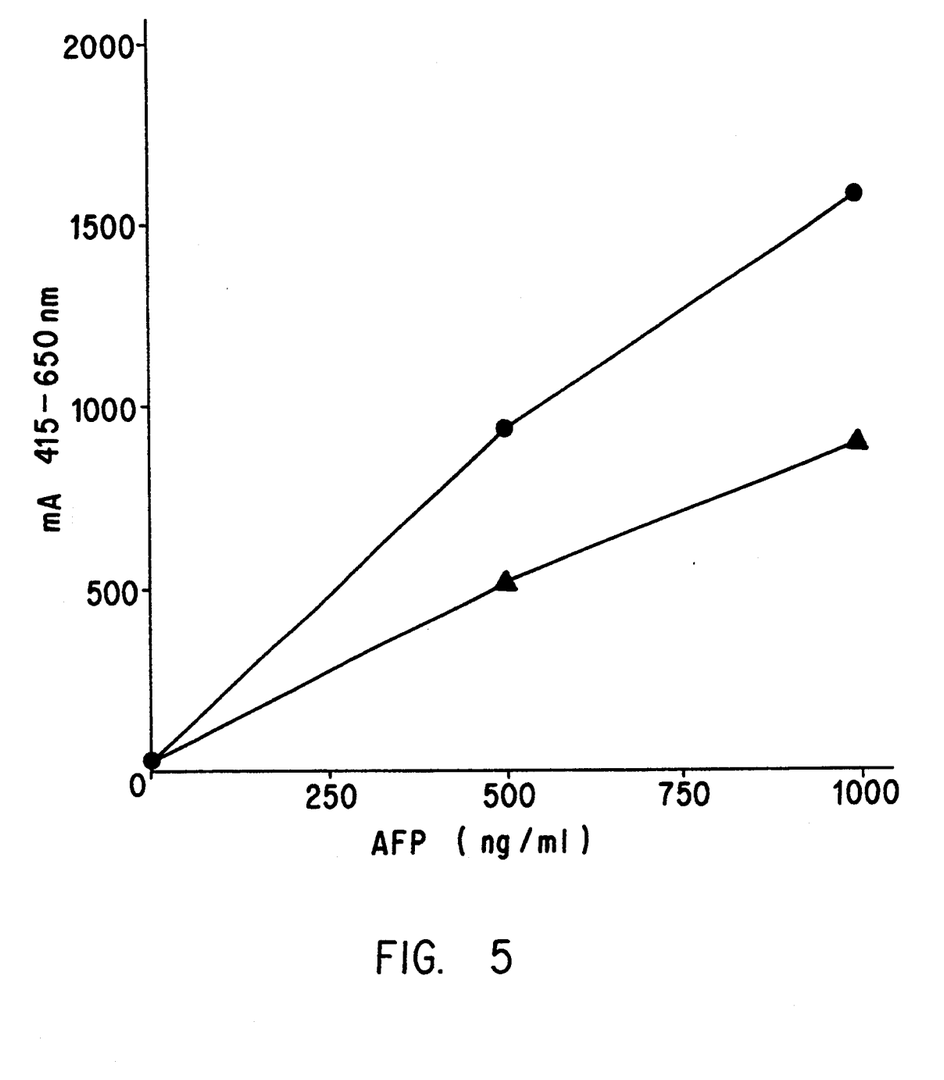
FIG. 5 is a calibration curve for an antigen (AFP) in a sample measured by enzyme immunoassay using Solid Phase I of the present invention employing a biotin-Fab' or a conventional avidin-immobilized solid phase in which the sensitivity in case of Solid Phase I of the present invention and the sensitivity in case of the conventional solid phase are compared to each other.

As is clear from the results shown in FIGS. 4 and 5, the immunoassay using Solid Phase I of the present invention had higher sensitivity than that of the immunoassay using the conventional avidin-immobilized solid phase by about 1.5 times in case of the biotin-OA and about 1.8 times in case of the biotin-Fab'.

EXAMPLE 11 [Immunoassay for carcinoembryonic antigen (CEA)]

(a) Preparation of biotin-Fab':

The desired biotin-Fab' (anti-CEA antibody) was prepared using the procedure in Example 1 except that an anti-CEA monoclonal antibody (MA3564F manufactured by Oriental Yeast K.K.) was used instead of the anti-AFP monoclonal antibody.

(b) Preparation of POD-Fab':

The desired POD-Fab' (anti-CEA antibody) was prepared using the procedure in Example 2 except that an anti-CEA monoclonal antibody (239-1 manufactured by Morinaga Seikagaku Kenkyusho) instead of the anti-AFP monoclonal antibody.

(c) Preparation of Solid Phase I of the present invention:

The procedures in Example 5 using the biotin-BSA were repeated to give Solid Phase I of the present invention. The procedures in Comparative Example 3 were also repeated to give the conventional avidin-immobilized solid phase as a control.

(d) CEA immunoassay:

Human CEA (manufactured by Morinaga Seikagaku Kenkyusho) was dissolved in human serum with no CEA and the solution was adjusted to CEA concentrations ranging from 0 to 50 ng/ml. This sample (50 µl) was poured into each well of the solid phase prepared in the above process (c), thereto was added an antibody solution (100 µl) prepared by adding 0.01M phosphate buffer (pH 7.0, containing 0.1M sodium chloride and 0.2% BSA) to-the biotin-Fab' (10 µg) and the POD-Fab' (15 IU) so that the total volume became 10 ml and the mixture was incubated at 37° C. for 15 minutes. After completion of the reaction, the reaction solution was removed by suction and a washing solution (physiological saline solution) was added to the well, followed by removal of the washing solution by suction. This washing procedure was repeated further four times. After washing, a substrate solution (ABTS 1 mg/ml, 0.01% hydrogen peroxide, in 0.1M citrate buffer, pH 4.2; 100 µl) was added to the resulting well and the mixture was reacted at 37° C. for 10 minutes. To the mixture was added 5 mM sodium azide (100 µl) as a reaction terminator and the absorbances at 415 nm (main) and at 650 nm (sub) were measured. The results are shown in FIG. 6 as a circle.

CEA immunoassay was also conducted using the above procedures except that the well of the conventional avidin-immobilized solid phase was employed instead of Solid Phase I of the present invention. The results are shown in FIG. 6 as a triangle.

Figure 6:
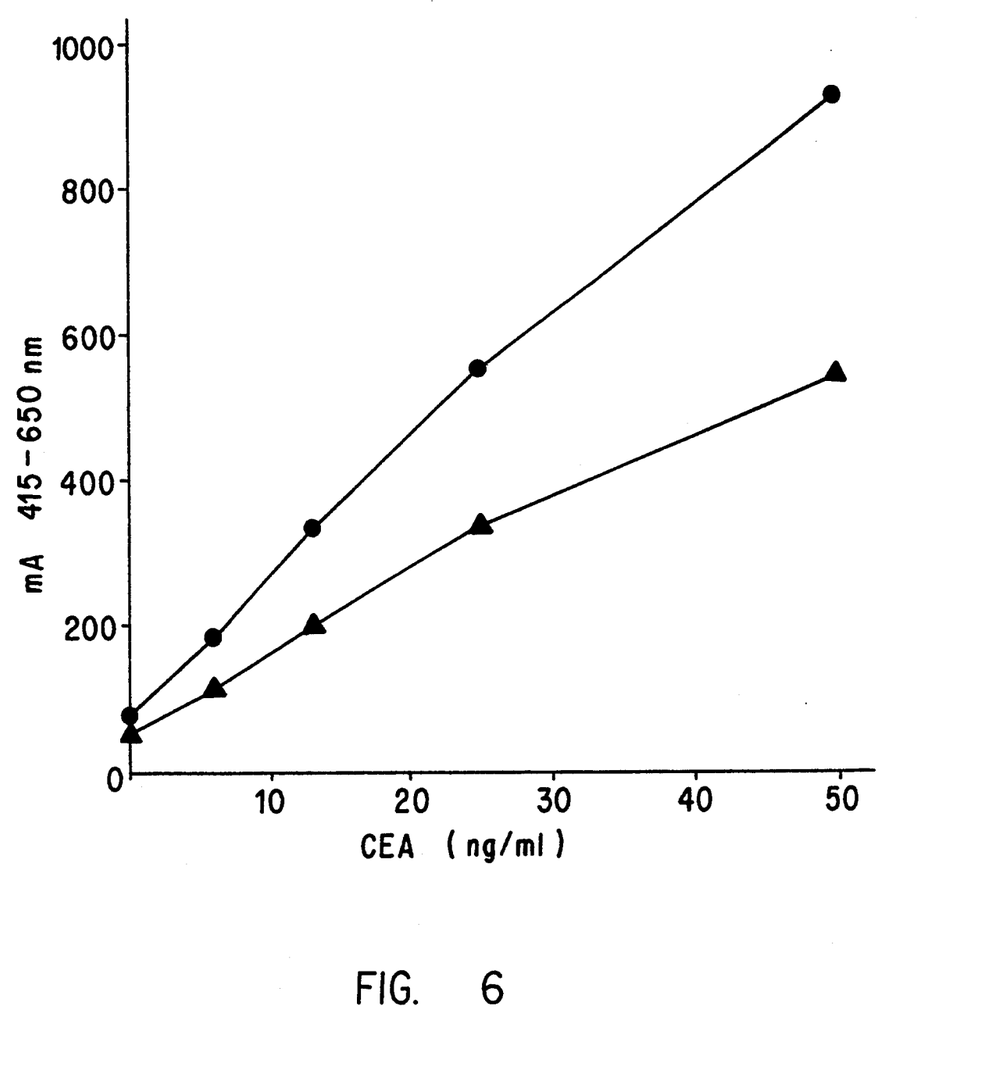
FIG. 6 is a calibration curve for an antigen (CEA) in a sample measured by enzyme immunoassay using Solid Phase I of the present invention employing a biotin-BSA or a conventional avidin-immobilized solid phase in which the sensitivity in case of Solid Phase I of the present invention and the sensitivity in case of the conventional solid phase are compared to each other.

As is clear from the results shown in FIG. 6, the Solid Phase I of the present invention similarly gave higher sensitivity (about 1.7 times) than that of the conventional avidin-immobilized solid phase in the CEA immunoassay.

(e) Correlation:

The correlation (n=20) between the immunoassay using Solid Phase I of the present invention and the conventional enzyme immunoassay (CEA EIA II "Abbott" commercially available from Dainabbott Co. Ltd.) was studied, and as a result, a good correlation was observed with a correlation coefficient of 0.964 and a regression formula of y=0,642x+2.0.

EXAMPLE 12 (AFP immunoassay using fluorescent substrate)

Figure 7:
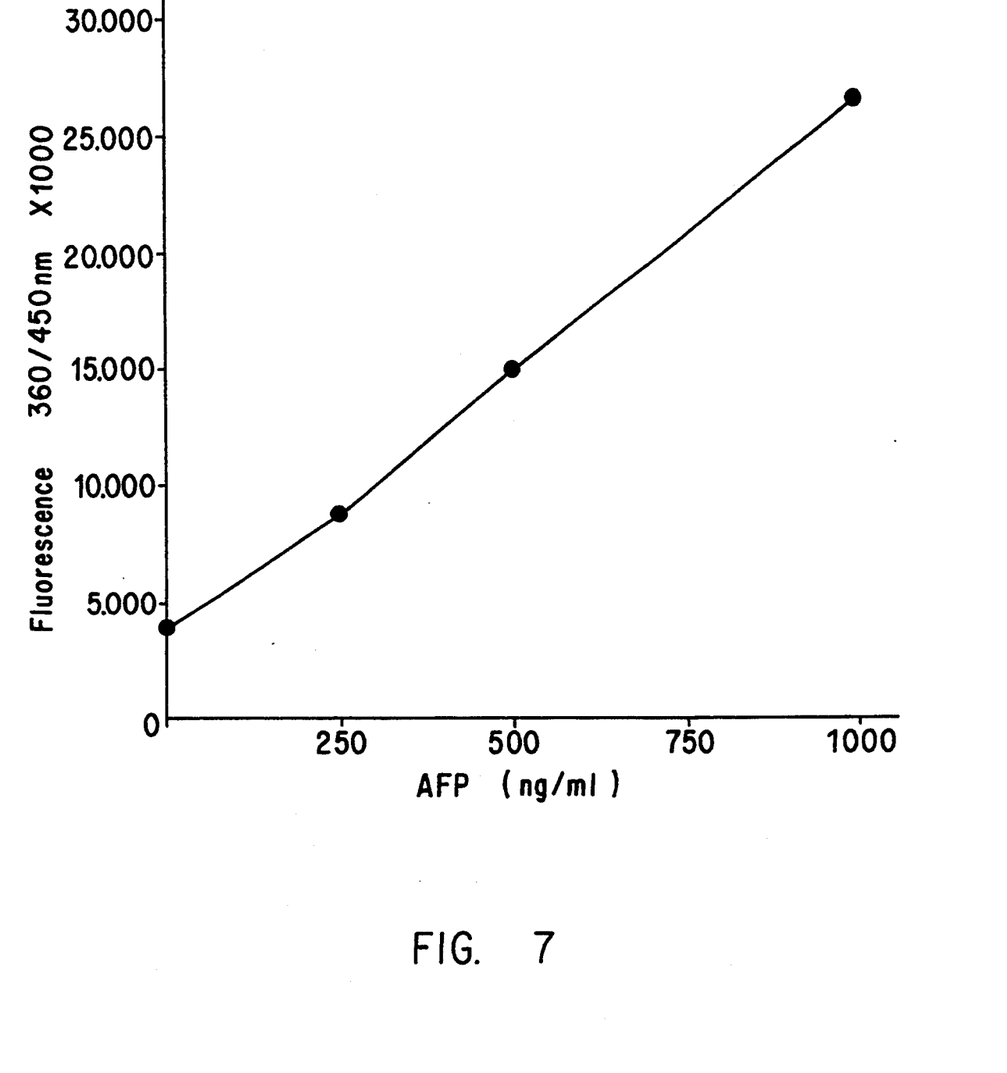
FIG. 7 is a calibration curve for an antigen (AFP) in a sample measured by enzyme immunoassay using Solid Phase I of the present invention employing a biotin-BSA and a fluorescent substrate as an enzyme substrate.

The AFP immunoassay was conducted in accordance with the procedures in Example 9 with the exception that the antigen-antibody reaction and the biotin-avidin reaction were carried out at 37° C. for 8 minutes; the enzyme reaction was carried out at 37° C. for 1 minute; 4-methylumbelliferyl-β-D-galactopyranoside (33.8 mg/l) was used instead of o-nitrophenyl-β-D-galactopyranoside as a substrate solution; and the absorbance measurement was done at the excitation wavelength of 360 nm and at the measuring wavelength of 450 nm. The results are shown in FIG. 7. As is clear from the results shown in FIG. 7, the good calibration curve was obtained.

It is found that the use of the fluorescent substrate realizes the measurement of an AFP concentration in a shorter period of time than the colorimetry in Example 9.

EXAMPLE 13 (Preparation of Solid Phase II of the present invention)

To Solid Phase I of the present invention prepared in accordance with the procedure in Example 5 (a) was added the biotin-Fab' solution [1.6 μg/ml in 10 mM phosphate buffer, pH 7.0, containing 0.15M NaCl and 0.1% BSA; 100 μl] prepared in Example 1 and the mixture was reacted at 37° C. for 1 hour to give Solid Phase II of the present invention for AFP immunoassay.

EXAMPLE 14 (Preparation of Solid Phase II of the present invention)

To Solid Phase I of the present invention prepared in accordance with the procedure in Example 5 (b) was added the biotin-Fab' solution [1 μg/ml in 10 mM phosphate buffer, pH 7.0, containing 0.15M NaCl and 0.1% BSA); 100 μl] prepared in Example 11 (a) and the mixture was reacted at 37° C. for 1 hour to give Solid Phase II of the present invention for CEA immunoassay.

EXAMPLE 15 (Preparation of Solid Phase II of the present invention)

To the conventional avidin-immobilized solid phase prepared in accordance with the procedure in Comparative Example 3 was added the biotin-Fab' solution [1.6 μg/ml in 10 mM phosphate buffer, pH 7.0, containing 0.15M NaCl and 0.1% BSA; 100 μl] prepared in Example 1 and the mixture was reacted at 37° C. for 1 hour to give Solid Phase II of the present invention for AFP immunoassay.

EXAMPLE 16 (AFP immunoassay)

Figure 8:
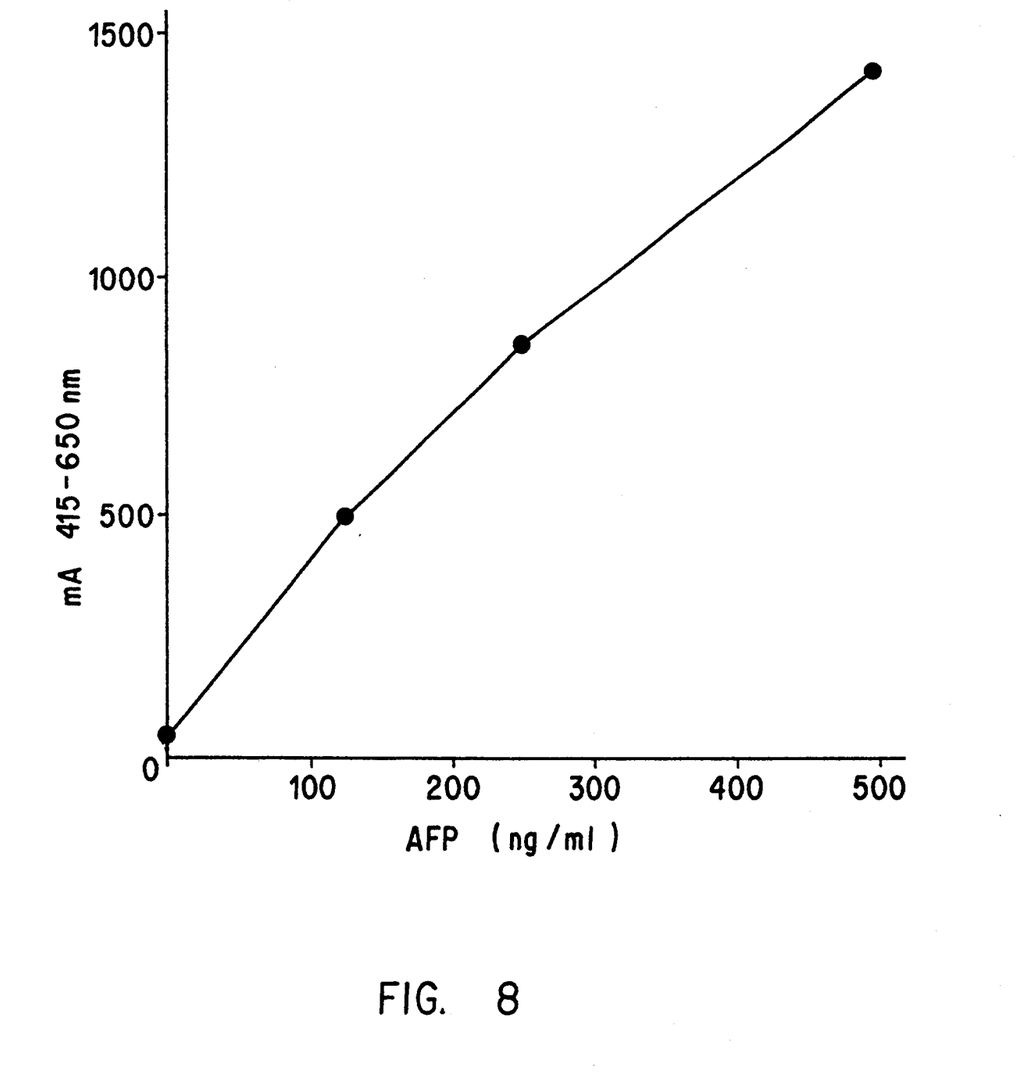
FIG. 8 is a calibration curve for an antigen (AFP) in a sample measured by enzyme immunoassay using Solid Phase II of the present invention employing a biotin-Fab'.

Human AFP (manufactured by Dako Co.) was dissolved in human serum with no AFP and the solution was adjusted to AFP concentrations ranging from 0 to 500 ng/ml. This sample (20 μl) was poured into each well of Solid Phase II of the present invention prepared in Example 13, and thereto was added an enzyme-labelled antibody solution (100 μl) prepared in Example 8 by adding 0.01M phosphate buffer (pH 7.0, containing 0.1M sodium chloride and 0.2% BSA) to the β-Gal-Fab' (20 U) so that the total volume became 10 ml, and the mixture was incubated at 37° C. for 15 minutes. Thereafter, the procedure in Example 9 was repeated to conduct the AFP immunoassay except that the absorbances at 415 nm (main) and at 650 nm (sub) were measured. The results are shown in FIG. 8.

EXAMPLE 17 (CEA immunoassay)

Figure 9:
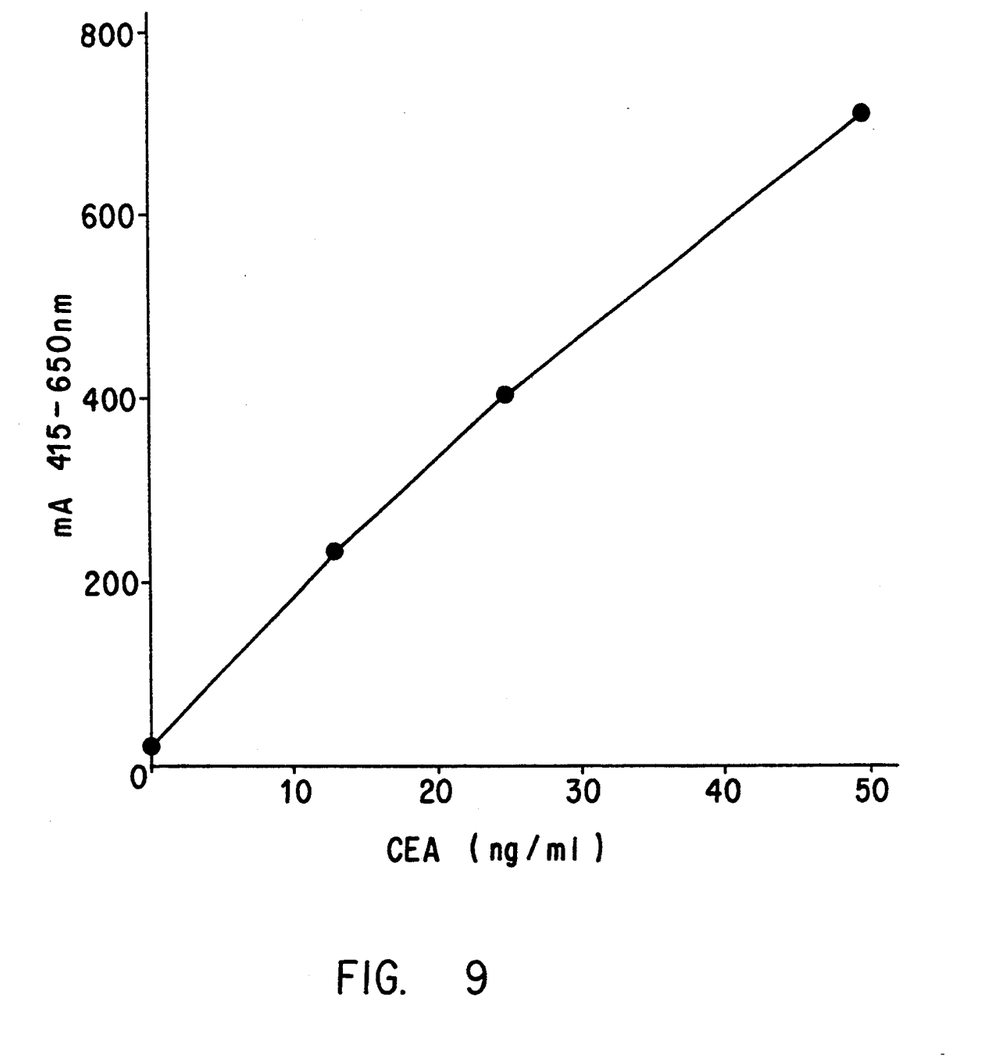
FIG. 9 is a calibration curve for an antigen (CEA) in a sample measured by enzyme immunoassay using Solid Phase II of the present invention employing a biotin-Fab'.

Human CEA (manufactured by Morinaga Seikagaku Kenkyusho) was dissolved in human serum with no CEA and the solution was adjusted to CEA concentrations ranging from 0 to 50 ng/ml. This sample (50 μl) was poured into each well of Solid Phase II of the present invention prepared in Example 14, and thereto was added an enzyme-labelled antibody solution (100 μl) prepared in Example 11 (b) by adding 0.01M phosphate buffer (pH 7.0, containing 0.1M sodium chloride and 0.2% BSA) to the POD-Fab' (15 IU) so that the total volume became 10 ml, and the mixture was incubated at 37° C. for 15 minutes. Thereafter, the procedure in Example 11 (d) was repeated to conduct the CEA immunoassay. The results are shown in FIG. 9.

EXAMPLE 18 (AFP immunoassay)

Human AFP (manufactured by Dako Co.) was dissolved in human serum with no AFP and the solution was adjusted to AFP concentrations ranging from 0 to 1000 ng/ml. This sample (20 μl) was poured into each well of Solid Phase II of the present invention prepared in Example 15, and thereto was added an enzyme-labelled antibody solution (100 μl) prepared in Example 8 by adding 0.01M phosphate buffer (pH 7.0, containing 0.1M sodium chloride and 0.2% BSA) to the β-Gal-Fab' (20 U) so that the total volume became 10 ml, and the mixture was incubated at 37° C. for 15 minutes. Thereafter, the procedure in Example 9 was repeated to conduct the AFP immunoassay except that the absorbances at 415 nm (main) and at 650 nm (sub) were measured. The results are shown in FIG. 10 as a circle.

The procedure in Comparative Example 3 using the conventional avidin-immobilized solid phase was also repeated to conduct the AFP immunoassay. The results are shown in FIG. 10 as a triangle.

Figure 10:
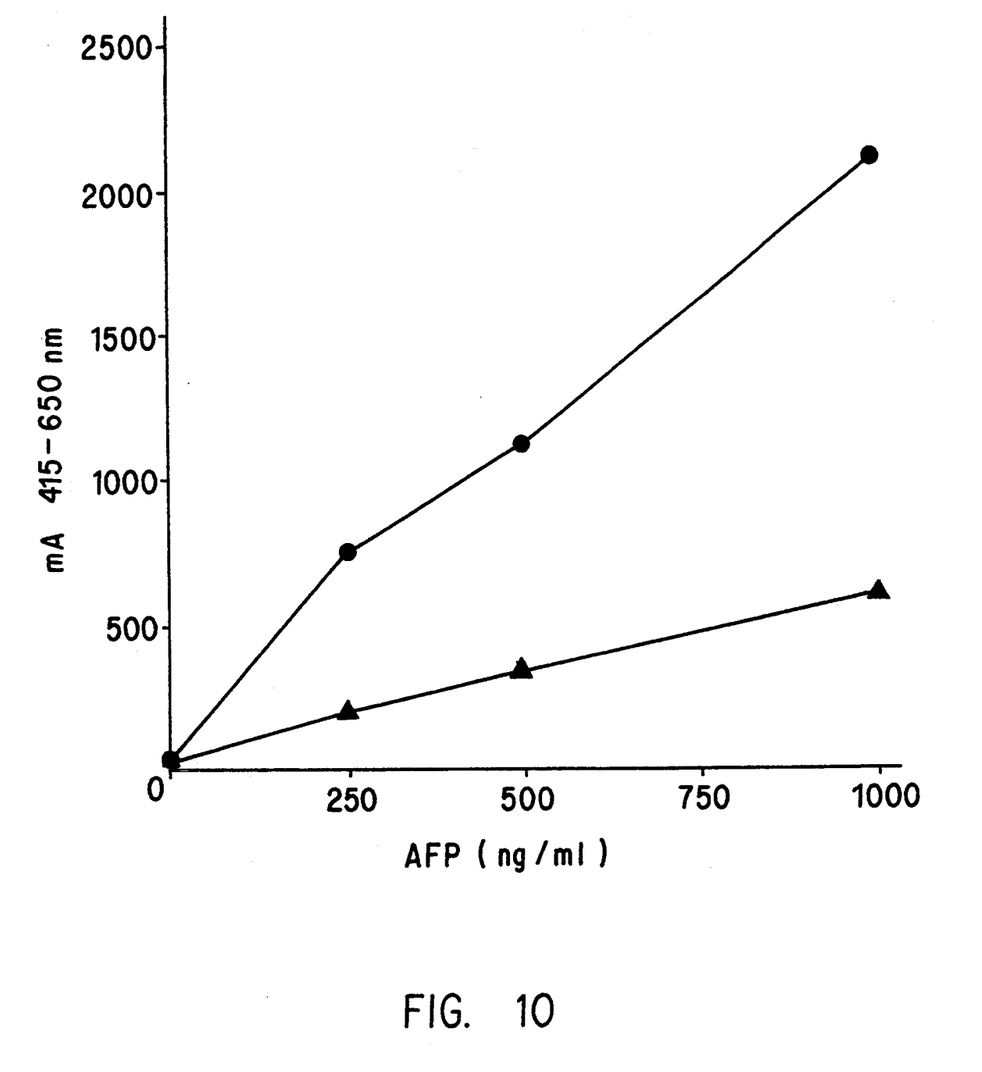
FIG. 10 is a calibration curve for an antigen (AFP) in a sample measured by enzyme immunoassay using Solid Phase II of the present invention employing a biotin-Fab' or a conventional avidin-immobilized solid phase in which the sensitivity in case of Solid Phase II of the present invention and the sensitivity in case of the conventional solid phase are compared to each other.

As is clear from the results shown in FIG. 10, the method using Solid Phase II of the present invention had about 3 times higher sensitivity than that using the conventional avidin-immobilized solid phase.

What is claimed is:

1. A method for determining the amount of an antigen in a sample, wherein the method comprises:
    (1) contacting the sample with (a) an enzyme-labelled antibody specific for the antigen, and (b) a pre-formed reagent comprising biotinylated Fab' fragments specific for the antigen immobilized on a solid phase through a first substance selected from the group consisting of avidin, streptavidin and derivatives thereof, wherein the Fab' fragments are biotinylated through thiol groups; and
    (2) determining the amount of antigen in the sample by measuring enzyme activity on the solid phase.

2. The method of claim 1 wherein the first substance is immobilized on the solid phase through a biotin derivative which is in turn bound to a second substance, wherein said second substance is absorbed or covalently bound to the solid phase, and wherein said second substance is a high molecular weight protein or polysaccharide which has a functional group reactive with the biotin derivative.

3. The method of claim 1 or 2 wherein the sample is contacted with the enzyme-labelled antibody and the pre-formed reagent simultaneously.

* * * * *